United States Patent [19]

Daugherty

[11] Patent Number: 4,474,780
[45] Date of Patent: Oct. 2, 1984

[54] CRYSTALLINE CEPHALOSPORIN

[75] Inventor: Byron W. Daugherty, Indianapolis, Ind.

[73] Assignee: Eli Lilly and Company, Indianapolis, Ind.

[21] Appl. No.: 516,220

[22] Filed: Jul. 22, 1983

[51] Int. Cl.$^3$ .................. A61K 31/545; C07D 501/22
[52] U.S. Cl. ........................................ 424/246; 544/30
[58] Field of Search ........................... 424/246; 544/30

[56] References Cited

U.S. PATENT DOCUMENTS

| | | | |
|---|---|---|---|
| 3,364,212 | 1/1968 | Patchett | 260/243 |
| 3,518,260 | 6/1970 | Spencer et al. | 260/243 |
| 3,560,489 | 2/1971 | Morin | 260/243 |
| 3,994,884 | 11/1976 | Wier | 260/243 C |

Primary Examiner—Paul M. Coughlan, Jr.
Attorney, Agent, or Firm—Charles W. Ashbrook; Arthur R. Whale

[57] ABSTRACT 7-(D-2-Naphthylglycylamido)-3-methyl-3-cephem-4-carboxylic acid tetrahydrate is a stable crystal form of a potent orally active gram positive antibiotic.

4 Claims, No Drawings

CRYSTALLINE CEPHALOSPORIN

BACKGROUND OF THE INVENTION 7-(D-2-Naphthylglycylamido)-3-methyl-3-cephem-4-carboxylic acid recently has been discovered to be a potent orally active antibiotic, displaying favorable pharmacokinetics and excellent gram positive activity. The compound is synthesized by reacting 7-amino-3-methyl-3-cephem-4-carboxylic acid (7-ADCA) with an N-protected 2-naphthylglycine acylating agent, followed by removal of the protecting group.

An object of this invention is to provide a new compound that is a stable crystalline form of 7-(D-2-naphthylglycylamido)-3-methyl-3-cephem-4-carboxylic acid.

SUMMARY OF THE INVENTION

This invention provides a crystalline composition of matter which is 7-(D-2-naphthylglycylamido)-3-methyl-3-cephem-4-carboxylic acid tetrahydrate. The crystals are large, dense and stable, and readily lend themselves to milling and grinding for adaptation to pharmaceutical formulation, particularly into solid dosage forms such as filled capsules and the like. The tetrahydrate of this invention is prepared by isolating 7-(D-2-naphthylglycylamido)-3-methyl-3-cephem-4-carboxylic acid from an aqueous medium.

DETAILED DESCRIPTION OF THE INVENTION

The crystalline compound provided by this invention has the following unique X-ray powder diffraction properties when measured with a 114.6 mm Debye-Scherrer camera containing a nickel filtered copper radiation of 1.5405 Å:

| Spacing, d: | Relative intensities, $I/I_1$ |
|---|---|
| 13.29 | .44 |
| 10.53 | .22 |
| 7.14 | .44 |
| 6.58 | 1.00 |
| 6.09 | .22 |
| 5.64 | .33 |
| 5.36 | .88 |
| 5.14 | .28 |
| 4.86 | .17 |
| 4.66 | .11 |
| 4.44 | .33 |
| 4.12 | .28 |
| 3.92 | .17 |
| 3.75 | .22 |
| 3.65 | .94 |
| 3.51 | .38 |
| 3.34 | .72 |
| 2.94 | .39 |
| 2.78 | .17 |
| 2.69 | .14 |
| 2.58 | .11 |
| 2.46 | .17 |
| 2.42 | .17 |
| 2.32 | .11 |
| 2.25 | .03 |
| 2.18 | .14 |
| 2.10 | .06 |
| 2.04 | .06 |

The compound provided by this invention can be prepared by reacting an acid addition salt of 7-(D-2-naphthylglycylamido)-3-methyl-3-cephem-4-carboxylic acid with a base such as sodium hydroxide or triethylamine so as to form the corresponding zwitterion, and crystallizing the zwitterion from water. For example, a salt such as the trifluoroacetic acid salt or the hydrochloric acid salt can be dissolved in water or a mixture of water and an organic solvent such as acetone or acetonitrile. A base such as aqueous ammonium hydroxide is added to adjust the pH to about 3 to about 5. The precipitate that forms is the tetrahydrate of this invention and is readily recrystallized from water.

The compound of this invention alternatively can be prepared by isolating the product of acylation of 7-amino-3-cephem-4-carboxylic acid (7-ADCA) from a solvent containing water. For example, 7-ADCA, typically as a silylated derivative, can be acylated with an N-protected D-2-naphthylglycine acid halide or mixed anhydride. The acylation generally is carried out in an organic solvent such as acetonitrile. Once the acylation is complete, the protecting groups can be removed by standard procedures and the solution of 7-(D-2-naphthylglycylamido)-3-methyl-3-cephem-4-carboxylic acid can be diluted with water so that it contains about 10 to 50% by volume of water, and the pH of the solution can be adjusted to about pH 3 to about 5. The crystalline product that forms is 7-(D-2-naphthylglycylamido)-3-methyl-3-cephem-4-carboxylic acid tetrahydrate.

The preparation of the compound of this invention is more fully described in the following detailed examples.

PREPARATION 1

Preparation of D,L-2-naphthylglycine (also named α-amino-α-(2-naphthyl)acetic acid)

A solution of 15.6 g (0.1 m) of 2-naphalde-hyde in 700 ml of 50% ethanol-water containing 14.7 g (0.3 m) of sodium cyanide and 38.4 g (0.4 m) of ammonium carbonate was heated at 50° C. for twenty hours. The reaction mixture was cooled and concentrated to about 400 ml by evaporation under reduced pressure, and then the solution was made acidic to pH 2.0 by the addition of conc. hydrochloric acid. The solid precipitate that formed was collected by filtration, washed with dilute hydrochloric acid, and then dried to afford 22.1 g of 4-(2-naphthyl)-2,4-imidazolidindione.

A solution of 5.0 g (22 mM) of the 4-(2-naphthyl)-2,4-imidazolidindione in 100 ml of 16% (v/v) aqueous sodium hydroxide was heated at reflux for two and one-half hours. The reaction mixture was then filtered, cooled, and washed with ethylacetate. The aqueous solution was next diluted with 6N hydrochloric acid to pH 5.1 and filtered to provide D,L-2-naphthylglycine. The reaction was repeated several times to produce larger quantities of the product.

A 10.0 g sample of D,L-2-naphthylglycine was purified by dissolving it into 125 ml of methanol containing 3.9 ml of acetyl chloride. The reaction mix-ture was filtered and the filtrate containing D,L-2-naphthylglycine hydrochloride was diluted with 5 ml of aniline. The precipitated product was collected by filtration and dried to give 7.0 g of D,L-2-naphthylglycine. m.p. 219°–221° C.

PREPARATION 2

Resolution of 2-naphthylglycine

A mixture of D and L 2-naphthylglycine (from Preparation 1) was reacted with di-tert.-butyl carbonate and sodium hydroxide to provide D,L-N-tert.-butoxycarbonyl-2-naphthylglycine. The t.Boc naphthylglycine was re-acted with optically pure α-aminoethylbenzene in the presence of N,N'-dicyclohexylcarbodiimide to provide N-(1-phenylethyl)-α-tert.-butoxycarbonylamino-α-(2-naphthyl)acetamide. Separation of the diastereomers by chromatography over silica gel afforded, following acid hydrolysis with 6N hydrochloric acid, D-2-naphthylglycine (OR −190°±3°) and L-2-naphthylglycine (OR=+190°±3°).

PREPARATION 3

Preparation of D-N-tert.-butoxycarbonyl-2-naphthyl-glycine

To a stirred solution of 10 g (50 mM) of D-2-naphthylglycine (from Preparation 2) in 100 ml of 1N sodium hydroxide were added 50 ml of tetrahydrofuran followed by 30 g (140 mM) of di-tert.-butyl carbonate. The reaction mixture was stirred at 24° C. for four hours. The product was isolated by first washing the reaction mixture three times with 50 ml portions of diethyl ether, and then the mixture was made acidic to pH 2.0 by the addition of conc. hydrochloric acid. The aqueous acid mixture was extracted several times with ethyl acetate, and the extracts were combined, washed with water, dried and the solvent was removed by evap-oration under reduced pressure to provide 12.8 g (85% yield) of D-N-tert.-butoxycarbonyl-2-naphthylglycine.

NMR (DMSO): δ 2.5 (s, 9H); δ 6.85 (s, 1H); δ 7.28–7.9 (m, 7H).

EXAMPLE 1

7-(D-2-Naphthylglycylamido)-3-methyl-3-cephem-4-carboxylic acid trifluoroacetate salt To a stirred suspension of 1.0 g (4.7 mM) of 7-amino-3-methyl-3-cephem-4-carboxylic acid (7-ADCA) in 25 ml of acetonitrile were added in one portion 3.7 ml (14.0 mM) of bis(trimethylsilyl)trifluoro-acetamide. The reaction mixture was stirred at room temperature until all solids had dissolved, thus indicating complete formation of the trimethylsilyl ester of 7-ADCA.

In a separate flask a solution of 1.35 g (4.5 mM) of D-N-tert.butoxycarbonyl-2-naphthylglycine (from Preparation 3) in 20 ml of acetonitrile containing 1.1 g (4.5 mM) of N-ethoxycarbonyl-2-ethoxy-1,2-dihydroquinoline (EEDQ) was stirred at room temperature for fifteen minutes. This solution was then added in one portion to the cold (0° C.) acetonitrile solution containing the trimethylsilyl ester of 7-ADCA from above. The reaction mixture was stirred for one hour at 0° C., and then warmed to room temperature. The solvent was removed by evaporation under reduced pressure to give an oil, and the oil was dissolved in ethyl acetate, washed two times with 1N hydrochloric acid, dried, and the solvent was removed by evaporation to provide 7-(D-N-tert.-butoxycarbonyl-2-naphthylglycylamido)-3-methyl-3-cephem-4-carboxylic acid as a foam.

The N-protected naphthylglycyl cephalosporin thus produced was dissolved in 5 ml of trifluoroacetic acid, and then the trifluoroacetic acid was removed by evap-oration under reduced pressure to provide, following precipitation from diethyl ether, 5.7 g of 7-(D-2-naphthylglycylamido)-3-methyl-3-cephem-4-carboxylic acid trifluoroacetate salt.

EXAMPLE 2

7-(D-2-Naphthylglycylamido)-3-methyl-3-cephem-4-carboxylic acid tetrahydrate A mixture of 5.7 g of the trifluoroacetic acid addition salt from Example 1 in 55 ml of 10% (v/v) water and acetonitrile was warmed to about 50° C. and then filtered to remove the undissolved solids. The filtrate was diluted with 1.8 molar ammonium hydroxide to pH 4.5. The precipitate that formed was collected by filtration and dried to give 3.15 g (72% yield) of 7-(D-2-naphthylglycylamido)-3-methyl-3-cephem-4-carboxylic acid tetra-hydrate.

EXAMPLE 3

The procedure of Example 1 was repeated using 5.0 g of optically active D-N-tert.butoxycarbonyl-2-naphthylglycine and 5.6 g of 7-ADCA to provide, following removal of the protecting groups, 6.8 g (80% yield) of D-7-(2-naphthylglycylamido)-3-methyl-3-cephem-4-carboxylic acid trifluoracetic acid salt. The salt thus formed was dissolved in 90 ml of aceto-nitrile and 10 ml of water. The pH of the solution was adjusted to 4.0 by addition of triethylamine, and the reaction mixture was stirred at 25° C. for twenty minutes. The mixture was filtered and the filtrate was concen-trated to dryness and the product was crystallized from water to give 2.9 g of 7-(D-2-naphthylglycylamido)-3-methyl-3-cephem-4-carboxylic acid tetrahydrate.

Analysis calc. for $C_{20}H_{19}N_3O_4S \cdot 4H_2O$; Theory: C, 51.16; H, 5.80; N, 8.95; S, 6.93; Found: C, 52.52; H, 5.47; N, 8.73; S, 6.83.

NMR (DMSOd$_6$): δ 1.9 (s, 3H); δ 4.8 (s, 1H); δ 4.9 (dd, 1H); δ 5.6 (dd, 1H); δ 7.49–7.99 (m, 7H).

EXAMPLE 4

Preparation of 7-(D-2-naphthylglycylamido)-3-methyl-3-cephem-4-carboxylic acid tetrahydrate D-2-Naphthylglycine sodium salt was protected as an enamine by reaction with methyl acetoacetate. A suspension of 102 g (317.7 mM) of the protected D-2-naphthylglycine sodium salt in 1000 ml of acetonitrile and 500 ml of N,N-dimethylformamide was cooled to −30° C. and stirred while 0.88 ml of methane sulfonic acid was added in one portion, followed by the addition of 0.90 ml of N,N-dimethylbenzylamine and 24.7 ml of methyl chloroformate. The reaction mixture was stirred at −30° C. for two hours, and was then diluted by dropwise addition of a solution of 68.5 g (302.8 mM) of 7-amino-3-methyl-3-cephem-4-carboxylic acid in 460 ml of acetonitrile containing 118.8 ml hexamethyldisilazane. The reaction mixture was stirred at −30° C. for about two hours following com-plete addition and then warmed to 0° C. The reaction mixture was diluted by addition of 320 ml of 1N hydro-chloric acid, followed by addition of 35.7 g of semi-carbazide hydrochloride. Ammonium hydroxide was added to adjust and main-tain the pH at 3.0 while the mixture was warmed to 22° C. The reaction mixture was further diluted by addition of 430 ml of water, and then de-colorized by stirring for fifteen minutes with 10.0 g of charcoal. The reaction mixture was filtered through hyflo filter aid and the filtrate was warmed to 40° C. The pH was adjusted to 4.0 by addition of 1N ammonium hydroxide, whereupon crystallization started. Crystallization continued for about thirty minutes, and then the pH was raised to 5.2 by addition of 1N ammonium hydroxide. The mixture was cooled to 20° C. and stirred for one hour and filtered. The filter cake was washed twice with 50 ml portions of water and air dried to give 110.8 g of 7-(D-2-naphthylglycylamido)-3-methyl-3-cephem-4-carboxylic acid tetrahydrate.

Analysis calc. for $C_{20}H_{19}N_3O_4S.4H_2O$; Theory: C, 51.16; H, 5.80; N, 8.97; S, 6.83; Found: C, 50.31; H, 5.62; N, 8.87; S, 6.89.

Karl Fisher water analysis: Theory: 15.3: Found: 13.73%.

NMR (TFA): $\delta$ 2.2 (s, 3H); 3.21 (q, 2H); 5.08 (d, 1H); 5.68 (m, 2H); 7.4–8.3 (m, 7H); 10.5 (s, 12H).

IR (KBr): 1766, 1751, 1696 $cm^{-1}$

UV ($CH_3OH$): $\lambda_{max}$ 227, $\epsilon$, 78,000, $\lambda_{max}$ 265, $\epsilon$, 12,000.

Titration (66% N,N-dimethylformamide/water) pKa 5.5, 7.5, 11.2.

The compound of this invention is useful as an oral antibiotic, particularly in the treatment of infections caused by gram-positive organisms such as *S. aureus, S. pyogenes* and *H. influenza*. The compound is also effective against anaerobic cocci such as *Peptostreptococcus anaerobius* and *Peptostrept. intermedius*. The compound is very well absorbed following oral administration, and its favorable pharmacokinetics make it particularly attractive as an oral treatment for upper respiratory infections.

The compound will be administered at a dose of about 0.5 to about 50 mg/kg of animal body weight, and more normally at a dose of about 1 to about 10 mg/kg. Such amounts will be administered to a human from once to about four times a day for the effective control and prevention of bacterial infections. A typical daily adult dose will be from about 200 to about 500 mg. per day.

The crystal form provided by this invention will be formulated for convenient oral or parenteral administration, and such formulation will contain about 0.1 to about 95 percent by weight of active ingredient. The compound will be mixed with typical pharmaceutical carriers and excipients such as corn starch, sucrose, microcrystalline cellulose, gelatin, and the like. The formulations will be molded into tablets or placed into gelatin capsules, or made into solutions or suspensions for convenient oral administration. The compound can also be formulated as a slow release long term dosage form employing conventional technology.

The crystal form provided by this invention is very stable for prolonged periods of time, yet is very well absorbed following oral administration. This is somewhat surprising since the compound is only minimally soluble in water. For example, the compound forms a saturated solution in water at 37° C. according to the following table:

| pH | Solubility, mg/ml |
|---|---|
| 1.2 | 8.6 |
| 2.0 | 1.7 |
| 3.0 | 0.2 |
| 4.0 | 0.2 |
| 5.0 | 0.2 |
| 6.0 | 0.3 |
| 7.0 | 0.8 |
| 7.5 | 1.2 |
| 8.0 | 4.1 |
| 8.5 | 7.5 |

I claim:

1. Crystalline 7-(D-2-naphthylglycylamido)-3-methyl-3-cephem-4-carboxylic acid tetrahydrate exhibiting essentially the following x-ray diffraction data:

| Spacing, d: | Relative intensities, $I/I_1$ |
|---|---|
| 13.29 | .44 |
| 10.53 | .22 |
| 7.14 | .44 |
| 6.58 | 1.00 |
| 6.09 | .22 |
| 5.64 | .33 |
| 5.36 | .88 |
| 5.14 | .28 |
| 4.86 | .17 |
| 4.66 | .11 |
| 4.44 | .33 |
| 4.12 | .33 |
| 3.92 | .17 |
| 3.75 | .22 |
| 3.65 | .94 |
| 3.51 | .38 |
| 3.34 | .72 |
| 2.94 | .39 |
| 2.78 | .17 |
| 2.69 | .14 |
| 2.58 | .11 |
| 2.46 | .17 |
| 2.42 | .17 |
| 2.32 | .11 |
| 2.25 | .03 |
| 2.18 | .14 |
| 2.10 | .06 |
| 2.04 | .06 |

2. A pharmaceutical formulation comprising an antibacterially effective amount of the compound of claim 1 admixed with a pharmaceutical carrier or excipient therefor.

3. A method of treating diseases of bacterial origin comprising administering an effective dose of the compound of claim 1.

4. The method of claim 3 wherein the compound is administered orally.

* * * * *